United States Patent [19]
Nakajima

[11] Patent Number: 4,748,970
[45] Date of Patent: Jun. 7, 1988

[54] ENDOSCOPE SYSTEMS
[75] Inventor: Shigeru Nakajima, Hachioji, Japan
[73] Assignee: Olympus Optical Co., Ltd., Japan
[21] Appl. No.: 50,096
[22] Filed: May 14, 1987
[30] Foreign Application Priority Data
  May 30, 1986 [JP] Japan .................................. 61-57684
[51] Int. Cl.⁴ .............................................. A61B 1/00
[52] U.S. Cl. ................................................... 128/4
[58] Field of Search ........................................ 128/4, 6
[56] References Cited
  U.S. PATENT DOCUMENTS
  4,261,343  4/1981  Ouchi et al. ............................ 128/4
  4,402,310  9/1983  Kimura ................................... 128/4
  4,548,197 10/1985  Kinoshita ............................... 128/4

FOREIGN PATENT DOCUMENTS
59-964101  4/1984  Japan .

Primary Examiner—William H. Grieb
Attorney, Agent, or Firm—Ostrolenk, Faber, Gerb & Soffen

[57]                 ABSTRACT

An endoscope system makes it possible to substantially unify the flow rates of fluid supply in each of a variety of endoscopes even when they are connected to means for fluid supply source common thereto.

13 Claims, 5 Drawing Sheets

ENDOSCOPE SYSTEMS

BACKGROUND OF THE INVENTION

The present invention relates to an endoscope system in which a plurality of endoscopes of different kinds are interchangeably connected to a fluid (liquid, water, air or gas) source or sources common thereto.

For an endoscope it is well known that air and liquid can be supplied with a single nozzle disposed in opposed relationship to an observation window by joining an air supply line and a water supply line which are arranged within the insertable portion of the endoscope, at the distal end thereof. In addition, air or a non-inflammable gas is supplied through the air supply line to the interior of a coelom to expand the coelom and thereby obtain a spacing between the observation window disposed at the distal end of the endoscope and the coelom wall.

Such an air supply a suction operation essentially forms part of the inserting technique during an procedure with an endoscope, so that the flow rate of the air supply must be controllable for proper insertability of an endoscope. In addition, since an oversupply of air may pain to patient or damage of a coelom tissue, the control of the flow rate of air supply is essential in an operation of an endoscope. This means that it is desirable for endoscopes to be used in the same coelom to have supply air with the same flow rate even when they differ in kind.

As a matter of fact, the length and diameter of the insertable portion of an endoscope and, accordingly, the resistance of the fluid supply pipe line for fluid supply varies with the kind or use of the endoscope, so in that the flow rate of fluid supply per unit time varies. The prior art has failed to take this into account.

By way of example, even with the same kind of an endoscope, the air supply flow rate of air supply varies when the endoscope has its insertable portion of different length, and even in general-purpose scopes of the same kind for the upper digestive canal, a normal scope and a small-diameter scope differ in their air supply flow rates.

As such, it is inconvenient to use an endoscope having the insertable portion of a different length and diameter since it has fluid supply pipe lines in a different length and diameter and there is a different flow rate of the fluid supply due to the different resistance of the pipe line.

A conventional method for changing the flow rate of an air supply is shown in Japanese Utility Model Publication Sho 58/1983—No. 18884 in which the air supply flow rate is controlled by leaking part of the air from the air supply through a leakage hole that is changeable in size. It is extremely difficult, however, to precisely control the flow rate by the leakage method. Another method for changing an air supply flow rate of air supply is shown in Japanese Laid-Open Utility Model Publication Sho 59/1984—No. 64101 in which a pressure device comprising a cylinder and a piston, is provided in a supply line or on a tank. With this method, it is also difficult to precisely control the flow rate.

It is conceivable to change the flow rate fluid supply flow rate in each endoscope with the conventional methods described above. However, in such a case it is necessary to adjust the flow rate in the endoscope in accordance with the resistance of the fluid supply line, necessitating excessive expenditure of time and effort. Accordingly, it is desirable to provide improved endoscopes which have the same flow rate fluid supply per unit time even when endoscopes that differ in kind are used.

In addition, it is to be particularly desired that the air supply flow rates are unified in a colonoscope and a sigmoidoscope for the colon, and in an esophagoscope, gastroscope, duodenoscope, enteroscope and general-purpose scope for the esophagus to the duodenum, when they are used in the same coelom.

A physician can recognize the difference in air supply flow rates of between 1300 ml/min and 1700 ml/min. In other words, it may be said that this difference of 30 percent is unacceptable. Accordingly, the difference in air supply flow rates not exceeding 15 percent, which is the half of 30 percent, can be practically considered to be the same flow rate.

As for an absolute fluid supply flow rate of fluid supply, the optimum value depends upon physician's technical skill. For example, some physicians like a comparatively small of fluid supply flow rate of approximately 1000 ml/min, that is, giving priority to preventing a danger due to oversupply of fluid and some others like a comparatively large flow rate of approximately 1700 ml/min, that is, giving priority to reducing an inspection period. Accordingly, it is desirable that an absolute fluid supply flow rate is made variable as by using a variable fluid pump. For the case where an endoscope for the upper digestive canal is substituted for a colonoscope, it is also desirable that both endoscopes have the same flow rate.

While the flow rate of air supply, which varies with particular kinds of endoscopes, is approximately 1500 ml/min, the water supply flow rate is several tens ml/min at the most, so that there won't be any trouble, such as oversupply of water, due to variation of the water flow rate. However, when spraying and ejecting air simultaneously, air flow is at the same rate as when only air is supplied. When cleaning a lens surface of an endoscope by spraying water, it is necessary to supply a predetermined amount of water at a substantially constant rate. Because there is a possibility of causing an oversupply of air into a coelom when cleaning the lens surface because of variations in the water flow rate it is desirable to unify the flow rates water supply.

OBJECT AND SUMMARY OF THE INVENTION

It is an object of the present invention to eliminate the above mentioned disadvantages by providing an endoscope system adapted to obtain the same flow rate of fluid (gas, air, water or liquid) supply per unit time even with endoscopes of different kinds.

According to the present invention, an endoscope system in which first and second endoscopes of different kinds are to be interchangeably connected to a fluid supply source common thereto, include means for unifying their fluid flow rates in the fluid supply line.

There are the following two methods of unifying the flow rates in principle.

(A) The output of common fluid supply source is fixed and the resistances of fluid supply lines of the first and second endoscopes are unified.

(B) The output of common fluid supply source is controlled in accordance with the resistance of fluid supply line in the endoscope body.

The method (A) of adjusting the resistance of fluid supply line is achieved by increasing or reducing the resistance of fluid supply for example, at a connector a, fluid supply line on the universal cord side, a changeover valve for fluids, a fluid supply line on the insertable portion side and a nozzle of an endoscope, at least in part thereof.

The method (B) of controlling the output of a fluid supply source is achieved by providing a control means for controlling the fluid pressure or flow rate.

Further, according to the present invention, it is possible to provide an endoscope system which gives the same fluid supply flow rate even when first and second endoscopes of different kinds are used. this arrangement is safe that a oversupply of fluid due to the difference in supplying time periods is hard to cause.

In addition, it will be understood that a non-inflammable gas can be supplied with the same effect as is obtained when air is supplied. Besides, in an endoscope in which air and a non-inflammable gas are selectively supplied thereto, it is possible to unify their flow rates. It is also to be noted that liquid such as a physiological saline solution or a medical fluid, which is harmless to a human body, may be used in the endoscope system of the present invention.

DETAILED DESCRIPTION OF PREFERRED EMBODIMENTS

Figure 1:
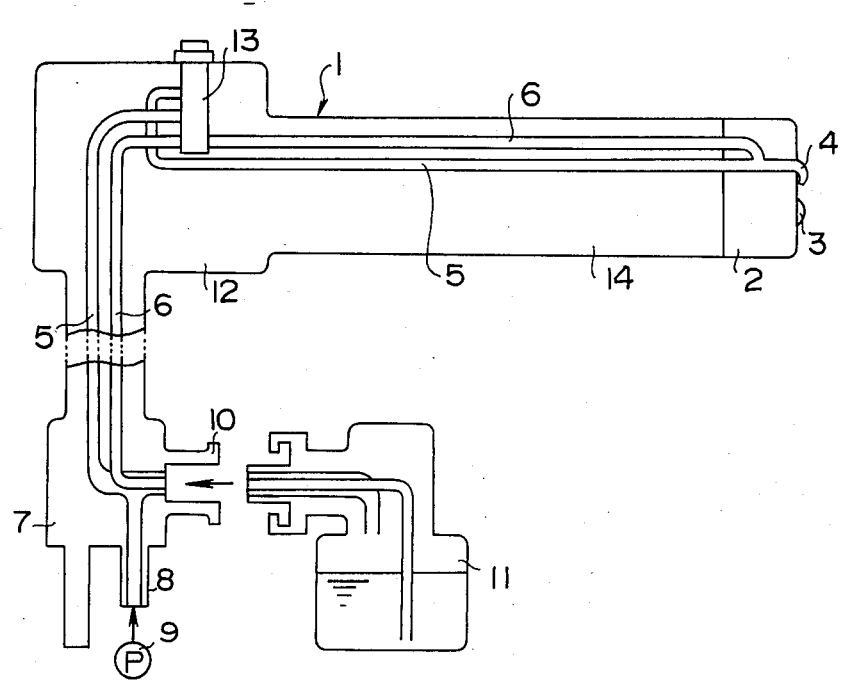
FIG. 1 is a schematic diagram showing air and liquid supply lines in an endoscope having the insertable portion of long length.
Figure 2:
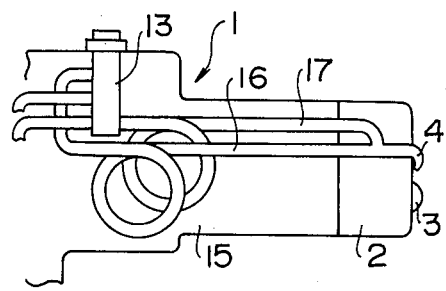
FIG. 2 is a schematic diagram showing a first embodiment of an endoscope system according to the present invention in which air and liquid supply lines of an endoscope having the insertable portion of short length.

In FIGS. 1 and 2, the distal end of an endoscope body 1 has an observation window 3, and a nozzle 4 in opposed relationship with the window 3. The nozzle 4 communicates with an air supply line 5 and a liquid supply line 6 which pass through the endoscope body 1. The supply lines 5, 6 join at the distal end 2. The air supply line 5 is connected through a mouthpiece 8 for air supply provided on a connector 7 of the endoscope body 1 to a pump 9. The liquid supply line 6 is connected through a mouthpiece 10 for liquid supply provided on the connector 7 to a water supply tank 11. A changeover valve 13 (see FIG. 6) for air and liquid supply is provided within an operating portion 12 along the fluid supply line.

The endoscope shown in FIG. 1 has its long insertable portion 14 connected to the endoscope body 1. The endoscope shown in FIG. 2 has its short insertable portion 15 connected to the endoscope body 1. An air supply line 16 and a liquid supply line 17 of the endoscope 1 having the short insertable portion 15 are made of the same material of the same diameter. However, parts of the air and liquid supply lines 16 and 17 are formed into loops so as to reduce the length in a straight line in proportion to the length shorter than that of this insertable portion 5. In the embodiment, the air and liquid supply lines 16, 17 are each provided with a loop which is shown in FIG. 2 as being in the run between the changeover valve 13 and the distal end 2. It will be understood that the looped portion may be between the changeover valve 13 and the connector 7.

An increment of the line resistance due to the line looping is adjusted by changing the length of the line. Thus, the resistances of the air and liquid supply lines 16, 17 are adjusted so as to be the same as those of the air and liquid supply lines 5, 6 shown in FIG. 1, respectively.

Endoscopes having their insertable portions of different lengths as shown in FIGS. 1 and 2 are used, according to circumstances, by interchangeably connecting to the liquid supply tank 11 and the air supply pump 9 common thereto. At this time, the line resistances of the air supply lines 5, 16 and the liquid supply lines 6, 17 are substantially the same, respectively, so that substantially the same flow rates per unit time for air and liquid supply can be obtained respectively even when the endoscopes are interchanged.

In the first embodiment, in which the endoscopes shown in FIGS. 1 and 2 use tubes of the same material of the same diameter, there is no need to prepare tubes of different diameters and, thus facilitating manufacturing of the supply lines.

Figure 3:
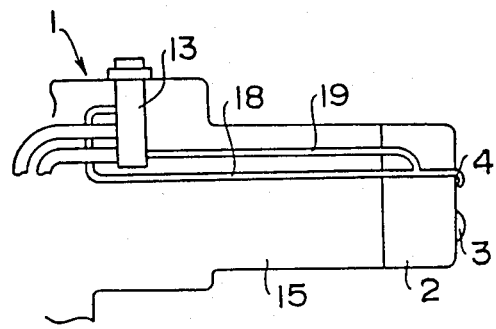
FIGS. 3, 4 and 5 are schematic diagrams respectively showing a second, a third and a fourth embodiments of an endoscope system according to the present invention showing air and liquid supply lines thereof.

FIG. 3 shows a second embodiment of the present invention, in which the resistances of supply lines are unified by changing the diameters thereof. The length of insertable portion 15 of an endoscope 1 shown in FIG. 3 is shorter than that of insertable portion 14 of the endoscope shown in FIG. 1 and therefore an air supply line 18 and a liquid supply line 19 are reduced in length according to the difference in length between both insertable portions 14, 15. However, the lines 18 and 19 are respectively reduced in diameter so as to unify their resistances to those of the lines 5 and 6. Accordingly, the endoscope 1 of the second embodiment can be reduced in diameter, facilitating its insertion.

In the second embodiment, the lines 18 and 19 in the insertable portion 15 are reduced in diameter over the whole length. It will be understood, however, that only parts of their lines or at least one part of lines in a universal cord or a connector may be reduced in diameter.

By way of example, when there are two kinds of endoscopes having their insertable portions of the same length, a normal size in diameter for an adult and a reduced size in diameter for a child, the latter must have an air supply line 5 of reduced diameter. In this case, at least part of the air supply line within a universal cord is made larger in diameter than that of the former so that the flow rate of air supply can be unified.

In addition, in first and second endoscopes having supply lines of different diameters and insertable portions of the same length, the first embodiment, FIG. 1, described above and fourth to seventh embodiments respective FIGS. 5, 7, 9, 10, which will be described hereinafter, may be applied thereto in order to unify their flow rates of air and liquid supply, respectively. Such an example is shown in FIG. 4.

Figure 4:
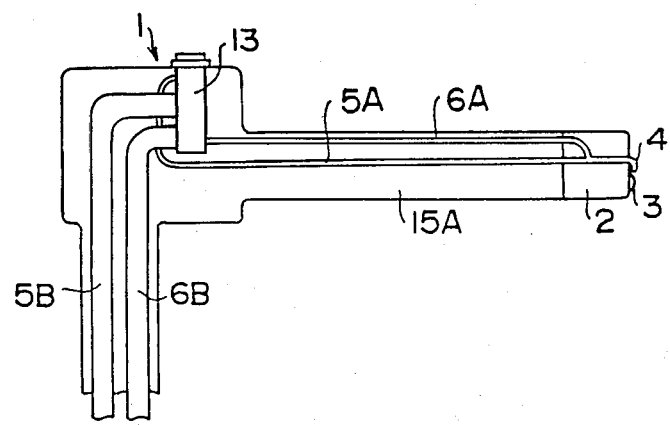

In FIG. 4, which shows a third embodiment of the present invention, an endoscope 1 has an insertable portion 15A of the same length as that shown in FIG. 1 and air, with, liquid supply lines 5A, 6A, respectively being of different sizes from those shown in FIG. 1, the line resistances of which are respectively unified. In the embodiment of FIG. 4, the insertable portion 15A is of reduced diameter and therefore the air and liquid lines 5A, 6A are of reduced diameters. In such a case, air and liquid supply lines 5B, 6B within an operating portion, a universal cord and a connector are increased in diameter part or the entire length of each of them. Conversely, when an endoscope has an increased diameter insertable portion, the line resistances may be unified by means similar to other embodiments of the present invention.

Instead of reducing the diameter of air supply line in an endoscope having a short insertable portion, it may be possible to positively increase the diameter of air supply line in an endoscope having a long insertable portion so as to unify the air flow rates at an increased value.

In addition, it may be possible to increase the length of universal cord of an endoscope having a short insertable portion in accordance with the difference in length between insertable portions. At this time, the lengthened universal cord may be a curl cord.

Figure 5:
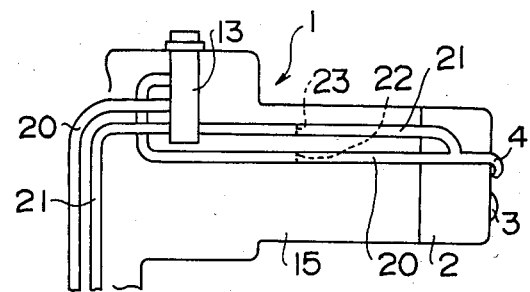

In FIG. 5, which shows a fourth embodiment of the present invention, an endoscope has the insertable portion shorter than that of the endoscope shown in FIG. 1. An air supply line 20 and a liquid supply line 21 are of the same diameter as those of the air supply line 5 and the liquid supply line 6 shown in FIG. 1 and are shortened in proportion to the difference in length between the insertable portions 14 and 15. However, restricted portions 22, 23 are provided within the air supply line 20 and the liquid supply line 21, respectively. While in the embodiment shown in FIG. 5 the restricted portions 22, 23 are provided downstream of the changeover valve 13 for air and liquid supply, it will be understood that they may be provided upstream of the changeover valve 13.

Figure 6:
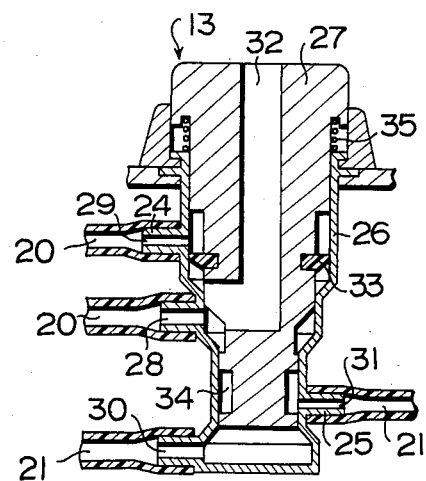
FIG. 6 is a section view showing an example of a changeover valve for air and liquid.

FIG. 6 is a section view of the changeover valve 13 for air and liquid supply. As shown, the present invention may also be modified such that a restricted portion 24 for air supply line and a restricted portion 25 for liquid supply line are formed on respective outlets 29, 31 of air and liquid supply lines in the changeover valve 13 so as to reduce the diameters of the outlets 29, 31, thereby increasing the resistances of the air and liquid lines 20, 21. The changeover valve 13 generally comprises a cylinder 26 and a piston 27 which fits into the cylinder 26. The cylinder 26 is provided with an air inlet 28 and an air outlet 29 which are connected respectively to the air supply line 20, and a liquid inlet 30 and a liquid outlet 31 which are connected respectively to the liquid supply line 21.

The changeover valve 13 normally operates in such a manner that air fed through the air supply line 20 leaks through the air inlet 28 and a through-hole 32 of the piston 27 to the atmosphere. When the through-hole 32 is blocked by holding down the head of the piston 27 with a hand, air fed from the air inlet 28 opens a check valve 33 to be fed through the restricted portion 24 of the air outlet 29 to the distal end 2. When the piston 27 is further depressed against the resilience of a spring 35 with the head of the piston 27 held down by a hand, the liquid inlet 30 communicates with the liquid outlet 31 through a peripheral groove 34 formed at the lower part of the piston 27 to supply liquid.

Figure 7:
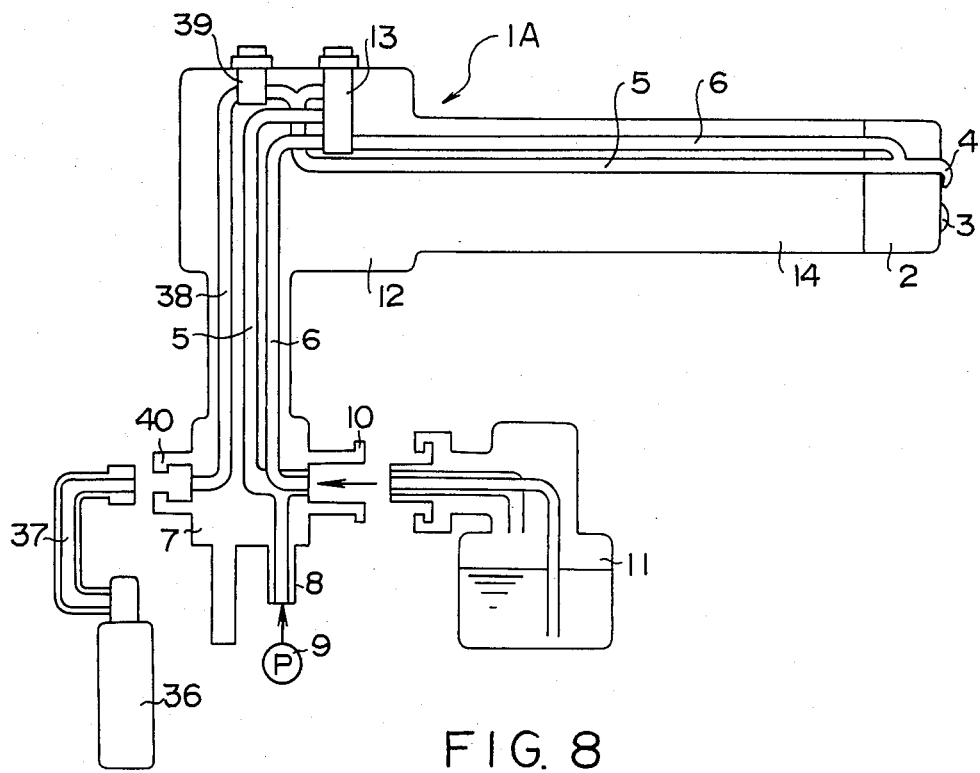
FIGS. 7 and 8 are schematic diagrams of a fifth embodiment of an endoscope system according to the present invention showing supply lines adapted to supply a gas in addition to air and liquid.
Figure 8:
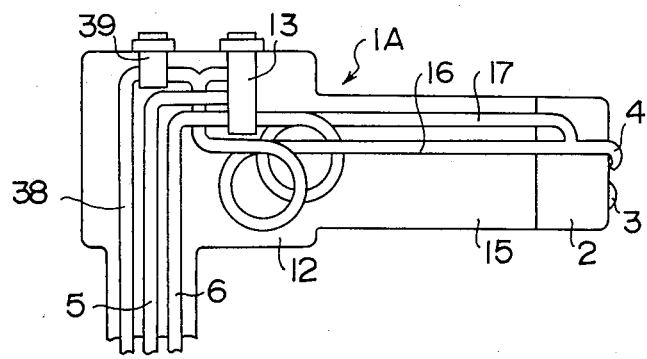

FIGS. 7 and 8 show a fifth embodiment of an endoscope 1A to which the present invention is applied and which contains a gas supply line 38 communicating with the air supply line 5, as occasion demands. A mouthpiece 40 for gas is provided on the connector 7 such that a gas tube 37 of a non-inflammable gas bomb 36 is connected thereto so as to supply gas from the mouthpiece 40 to the gas supply line 38. The gas supply line 38 communicates through a gas supply valve 39 for closing and opening the gas supply line 38 with the air supply line 5, within the insertable portion 12 and downstream of the changeover valve 13 for air and liquid supply. The gas supply line 38 can supply gas through valve 13 and downstream of the changeover valve 13 and the air supply line 5 to a coelom by depressing the valve 39. In an endoscope as shown in FIG. 8, when an air supply line 16 and a liquid supply line 17 are formed into loops in the same manner as in the first embodiment (FIG. 2) such that their diameters and lengths and, accordingly, their line resistances are respectively unified to those of the supply lines shown in FIG. 1, it is possible to make the flow rate of a gas supply constant by keeping gas supply pressure from bomb 36 constant with a regulator (not shown) provided on the non-inflammable gas bomb 36. Also, it may be possible to make the flow rate of a gas supply constant with a structure similar to those of the embodiments of second, fourth, sixth and seventh of the present invention.

In addition, it is possible to unify the flow rates of air and gas supplies by equalizing an air supply pressure of the pump 9 (FIG. 1) and a gas supply pressure of the gas bomb 36, which are connected to the endoscope 1A. When there is a difference between a preset output pressure of the bomb 36 and an output pressure of the pump 9, their flow rates of air and gas may be unified by changing their line resistances so as to balance the difference in resistance as in the other embodiments of the present invention.

Further, it is to be noted that the line resistances may be unified by changing the size of an outlet of the nozzle 4, though not shown. Namely, the nozzle 4 of an endoscope having an increased line resistance (FIGS. 1 and 7) is increased in its inner diameter and the nozzle 4 of an endoscope having a reduced line resistance is reduced in its inner diameter. In addition, when the nozzle 4 is made removable from the distal end 2, the flow rate of air supply can be adjusted by preparing nozzles of various sizes and properly selecting out of them. This is conveniently achieved only by changing nozzles. However, the supply line whose flow rate is adjusted as in first, second, third and fourth embodiments, has the disadvantage that when it goes wrong for some reason its repair is troublesome.

While the aforesaid embodiments have the arrangement in which an output of air or liquid supply is fixed and the line resistance in the endoscope body is substantially unified, the following embodiments have the arrangement in which an output of air supply or liquid supply is controlled in accordance with the line resistance in the endoscope body.

Figure 9:
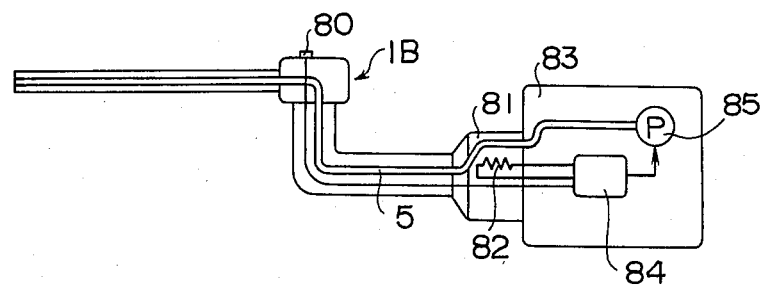
FIG. 9 is a schematic diagram of a sixth embodiment of an endoscope system according to the present invention.

FIG. 9 shows a sixth embodiment of the present invention, which automatically detects the kind of an endoscope and thereby controls an air or a liquid supply pressure. A resistor 82 for detecting the kind of an endoscope is arranged within a connector 81 which is connected to an endoscope body 1B which includes an air supply switch 80 for operating a controller 84. When the connector 81 is connected to an electric and light source 83, the controller 84 detects the kind of an endoscope by the resistance value of the resistor 82 and controls an output of air supply pressure to an air supply line 5 of an air pump 85 so as to assure a preset pressure for the kind of an endoscope.

Means for detecting a kind of endoscope and controlling a supply pressure in the sixth embodiment shown in FIG. 9 will be described in a practical manner as follows.

A first means is that endoscopes having different lengths or diameters are classified into several groups each having the line resistances of approximate values to detect the kind of endoscopes. In this case, it is preferable to classify endoscopes into groups with each group extending over an interval of approximately 15% (in the flow rate) the change of which is too small for an operator to notice.

With such means, it is possible to immediately take measures to a newly added kind of endoscope since the classification of all kinds of endoscopes are easily effected, whereas otherwise accommodation to each of all kinds of endoscopes needs a large scale and expensive apparatus for detection and control.

A second means is that a resistor for decision in kind which is built in each kind of endoscopes is made variable to construct part of a control circuit such that the output of an air pump is controlled by the variable resistor itself. With such an arrangement, it is possible to adjust the flow rate of each endoscope in a precise manner and to deal with a new kind of endoscope in a satisfactory manner.

A third means is that a variable valve for controlling the flow rate is provided at the outlet of an air pump is employed instead of controlling an air pump itself. With such an arrangement, it is possible to adjust the flow rate even when it exceeds the stable operation range of an air pump.

Further, it is to be noted that in the embodiments described above a physiological saline solution and a medical liquid, and not merely water, are applicable as a liquid to be supplied.

Thus, the air or liquid flow rates may be unified by controlling the output of the air or liquid supply source to endoscopes having the insertable portions 14 (15) different in length and, accordingly, the different resistances, without unifying the resistances.

Figure 10:
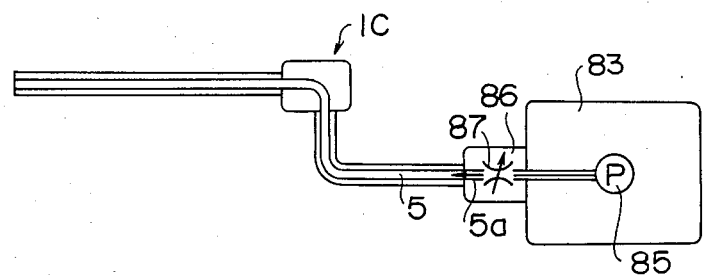
FIG. 10 is a schematic diagram of a seventh embodiment of an endoscope system according to the present invention.

FIG. 10 shows a seventh embodiment of the present invention, wherein controls for the flow rate of the air supply provided by air pump 85 are within the electric and light source 83 according to the kind of an endoscope. A variable orifice 87 is provided in air supply line 5a disposed within a connector 86 connected to an endoscope body 1C so as to adjust the orifice 87. The adjustment may be externally or previously made to each kind of endoscopes. In addition, a fixed orifice may be selectively used for each kind of endoscope and the orifice may be disposed at any position within an operating portion, for example, of an endoscope, not within the connector 86.

It will be understood that the present invention is applicable to normal endoscopes including an electronic endoscope and a fiberscope.

It will be further understood that while the aforesaid embodiments are described regarding two cases where the insertable portions differ in length, the present invention not limited to these, but is also applicable to any endoscopes of different kinds.

What is claimed is:

1. An endoscope system comprising:
   a plurality of endoscopes of different kinds having fluid supply lines;
   first means for a fluid supply source to be interchangeably connected to and common to said endoscopes; and
   second means for substantially unifying the flow rates of the fluid supply per unit time in the fluid supply lines of said endoscopes.

2. An endoscope system according to claim 1, in which said second means make the resistances of said fluid supply lines substantially equal.

3. An endoscope system according to claim 2, in which the resistances of said lines are made adjustably equal by forming the line tubes of the same material and diameter into loops in part of the lines.

4. An endoscope system according to claim 2, in which the resistances of said lines are made substantially equal by changing the inner diameters of said fluid supply lines at least in part of the supply lines.

5. An endoscope system according to claim 2, in which the resistances of said lines are made substantially equal by providing a restricted portion in part of the fluid supply lines.

6. An endoscope system according to claim 2, in which the resistances of said lines are made substantially equal by changing the inner diameters of the outlets of nozzles provided at the distal ends of insertable portions in endoscope bodies for communicating with the fluid supply lines.

7. An endoscope system according to claim 1, in which said unifying means control the output of said first means for fluid supply source in accordance with the difference between the line resistances of the fluid supply lines.

8. An endoscope system according to claim 7, in which controlling the outputs of said first means is effected by providing a variable orifice in the fluid supply line.

9. An endoscope system according to claim 7, in which said output control is effected by providing a variable orifice in the fluid supply line.

10. An endoscope system according to claim 1, in which said second means forms a restricted portion at the outlet of a changeover valve for fluid supplies disposed in the fluid supply line of the endoscope.

11. An endoscope system according to claim 1, in which said fluid supply source means includes source means for supplying air or gas.

12. An endoscope system according to claim 1, in which said fluid supply source means includes source means for supplying water.

13. An endoscope system according to claim 1, in which when air and gas supply source means are provided as said fluid supply source means, and means for substantially unifying the flow rates of the air and the gas supplies is included.

* * * * *